United States Patent [19]
Gartner et al.

[11] Patent Number: 5,633,316
[45] Date of Patent: May 27, 1997

[54] SURFACE CROSSLINKED AND SURFACTANT COATED ABSORBENT RESIN PARTICLES AND METHOD OF PREPARATION

[75] Inventors: Herbert Gartner, Baden-Baden; Josef Burgert, Achern-Fautenbach, both of Germany

[73] Assignee: The Dow Chemical Company, Midland, Mich.

[21] Appl. No.: 866,628

[22] Filed: Apr. 10, 1992

[30] Foreign Application Priority Data

Apr. 15, 1991 [GB] United Kingdom .................... 9107952

[51] Int. Cl.$^6$ .............................. C08B 30/00; C08F 6/00
[52] U.S. Cl. ..................... 525/54.32; 525/329.1; 525/329.4; 525/330.1; 527/311; 527/312; 527/314
[58] Field of Search ...................... 527/300, 311, 527/312, 313, 314; 525/54.32, 329.1, 329.4, 330.1

[56] References Cited

U.S. PATENT DOCUMENTS

| | | | |
|---|---|---|---|
| 3,661,815 | 5/1970 | Smith | 525/54.32 |
| 4,093,776 | 6/1978 | Aoki et al. . | |
| 4,734,478 | 3/1988 | Tsubakimoto | 527/300 |
| 4,742,086 | 5/1988 | Masamizu et al. | 521/62 |
| 5,057,580 | 10/1991 | Fock et al. | 525/329.5 |
| 5,164,459 | 11/1992 | Kimura et al. | 525/384 |

FOREIGN PATENT DOCUMENTS

| | | |
|---|---|---|
| 233067 | 2/1987 | European Pat. Off. . |
| 248437 | 6/1987 | European Pat. Off. . |
| 0450924 | 4/1991 | European Pat. Off. . |
| 0450924 | 10/1991 | European Pat. Off. . |
| 5684632 | 12/1979 | Japan . |
| 58-032641 | 2/1983 | Japan . |
| 04246403 | 9/1992 | Japan . |
| 2119384 | 4/1983 | United Kingdom . |
| 2162525 | 7/1985 | United Kingdom . |
| 2231573 | 4/1990 | United Kingdom . |

*Primary Examiner*—Jeffrey C. Mullis
*Attorney, Agent, or Firm*—Thomas A. Ladd; Norman L. Sims

[57] ABSTRACT

The invention is surface crosslinked particles of water absorbing resin comprising particles of a carboxyl containing water-absorbent resin; wherein the particles of the carboxyl containing water-absorbent resin are crosslinked at or near the particle surface by a polyhydroxy compound capable of reacting with the carboxyl moieties of the water-absorbent resin, and the particles have coated on or bound to the surface a nonionic surfactant having an HLB of from 3 to 10.

Additionally a process for the preparation of such surface crosslinked and surfactant coated absorbent resin particles is disclosed. Further disclosed is a water-absorbent structure comprising a synthetic or natural fiber or paper based woven or nonwoven carrier structure and surface crosslinked and surfactant coated water-absorbent resin particles of this invention.

5 Claims, No Drawings

SURFACE CROSSLINKED AND SURFACTANT COATED ABSORBENT RESIN PARTICLES AND METHOD OF PREPARATION

BACKGROUND OF INVENTION

This invention relates to surface crosslinked and surfactant coated water-absorbent resin particles. It further relates to an improved method for preparing surface crosslinked and surfactant coated water absorbent resin particles. In another embodiment, the invention relates to absorbent structures incorporating the absorbent resin particles of this invention.

Water absorbent resin particles (also referred to as superabsorbent polymers) are primarily used in personal care products to absorb body fluids, for example baby diapers, adult incontinence products, feminine hygiene products, and the like. In this application, the absorbent resin particles are incorporated into absorbent structures, for example synthetic and natural fiber or paper based woven and nonwoven structures, and toughened masses of fibers, such as fluff pads. The materials used in such structures can instantaneously absorb aqueous fluids and distribute them over the whole absorbent structure, in the case of fiber based materials by capillary forces. The structures, in the absence of water-absorbent resin particles, have limited absorption capacity, and are very bulky due to the large amount of material needed to provide acceptable absorption capacity. Further, the absorbent structures do not retain fluid under pressure. A means for improving the absorbency characteristics is to incorporate in the absorbent structures water absorbent resin particles which imbibe fluid to form a swollen hydrogel material, see U.S. Pat. No. 4,610,678 (incorporated herein by reference). This hydrogel serves to retain the absorbed fluid even under pressure and gives the absorbent structure a "dry feel" even when wetted. In order to reduce the bulk of absorbent structures containing water absorbent resin particles, large volumes of the absorbent structure material can be replaced with small volumes of absorbent resin particles. The absorbent resin particles must quickly absorb fluids and retain such fluids to prevent leakage.

Water-absorbing resins known in the art include carboxyl-containing resins selected from the group consisting of a hydrolyzate of a starch-acrylonitrile graft polymer, a partially neutralized product of a starch-acrylic acid graft polymer, a saponification product of a vinyl acetate-acrylic ester copolymer, a hydrolyzate of an acrylonitrile copolymer, a crosslinked product of a hydrolyzate of an acrylamide copolymer, a hydrolyzate of an acrylamide copolymer, a crosslinked product of a hydrolyzate of an acrylamide copolymer, a partially neutralized product of polyacrylic acid, and a crosslinked product of partially neutralized polyacrylic acid. These water-absorbing resins are well known in the art. For example, the hydrolyzate of a starch-acrylonitrile graft polymer is disclosed in U.S. Pat. No. 3,661,815 (incorporated herein by reference); the neutralization product of a starch-acrylonitrile acid graft polymer is disclosed in U.S. Pat. No. 4,076,663 (incorporated herein by reference); the saponification product of a vinyl acetate-acrylic ester copolymer is disclosed in Japanese Laid-Open Patent Publication No. 14689/1977 (incorporated herein by reference); the hydrolyzate of an acrylonitrile copolymer and the hydrolyzate of an acrylamide copolymer are disclosed in Japanese Patent Publication 15959/1978 (incorporated herein by reference); the crosslinked products of these hydrolyzates and a self-curable poly(sodium acrylate) obtained by inverse phase suspension polymerization are disclosed in U.S. Pat. No. 4,093,776 (incorporated herein by reference); and the crosslinked product of partially neutralized polyacrylic acid is disclosed in Japanese Laid-Open Patent Publication 84304/1980 (incorporated herein by reference).

Japanese Laid-Open Publication 84632/1981 (incorporated herein by reference) discloses an absorption agent consisting of a crosslinked poly(alkali metal acrylate) material obtained from (A) 0.01–10 parts by weight of a water-soluble and/or water dispersible surfactant (B) 0.005–20 parts by weight of a water soluble polyvalent alcohol per 100 parts by weight of (C) an acrylate salt based polymer composed from 10–40% by mole of acrylic acid and 60–90% by mole of acrylic acid alkali metal salt where the said acrylate salt based polymer (C) is solution polymerized in an aqueous solution at a concentration of at least 30% by weight to form a gel like water containing polymer which is subsequently heated and dried.

In conventional water-absorbent resins increasing the water-absorption capacity results in an increase in the fraction of water-soluble polymer present. At the same time the gel strength of the swollen gel, its absorption capacity under pressure and absorption speed is reduced. The water absorbent resin tends to agglomerate upon wetting, and such agglomeration results in a reduction of its absorption capacity. In absorbent structures containing such water absorbent resins, when agglomeration occurs after wetting gel blockage can result which prevents transport of fluids within the absorbent structure. This is a particular problem when a large fraction of the absorbent structure is replaced with water absorbent resin particles to prepare a thin absorbent device.

Several approaches are known for improving the absorption characteristics of aqueous fluid absorbent resins. Several focus on polymer post treatment, more specifically polymer surface modification, i.e. post surface crosslinking. EP 0,248,963 (incorporated herein by reference) describes a process of polymer post treatment by which the surface of a water-absorbent resin is treated with polyquarternary amines to increase the absorption rate significantly and the adsorption under load (AUL) by 10%. In this process the polyquarternary amines are applied as solutions in methanol. A separate blending operation is required to evenly distribute the polyquaternary amine evenly throughout the resin.

EP 0,248,437 (incorporated herein by reference) describes a process for polymer surface post crosslinking in which an aqueous solution of a water soluble peroxide radical initiator is sprayed onto the surface of the water absorbent resin particles and the coated particles are heated. Additional surface crosslinking is claimed leading to a product of improved water absorbency and water absorption rate. It is disclosed that the uniformity of penetration of the aqueous solution into the surface of the absorbent polymer may be improved in this process by use of a water soluble organic solvent such as methanol. A problem with this process is that high levels of peroxide radical initiators discolor partly neutralized polyacrylic acid and increase the low molecular weight water soluble fraction of this product if it is subjected to heat.

A process is disclosed in DE 3,713,601 A1 (incorporated herein by reference), in which surface crosslinking is obtained by the addition of a crosslinker of glycidyl- or polyglycidyl compounds. These crosslinking agents irritate the human skin, and may be harmful to human health.

A polymer post-treatment process is disclosed in GB 2,119,384, (DE 3,523,617 A1) (incorporated herein by reference) in which improvement of product properties is claimed by mixing absorbent resin powder with crosslinkers, preferably polyalcohols, like glycerol, a solvent and water, and heating this mixture to temperatures in the range of 90°–300° C. It is claimed that this post treatment reduces the agglomeration of the absorbent resin when wetted, increases its speed of water absorption and water retention, improves the flowability and reduces the dust. This process has some disadvantages. Traces of water are quickly absorbed by superabsorbent polymers, rendering it difficult to mix additives which are applied as an aqueous solution, with the dry, powdered superabsorbent. Addition of an aqueous solution to the polymer powder results in particle agglomeration, and when the agglomerated particles are subjected to heat, they form hard clusters which make additional processing such as breaking and screening necessary. It is disclosed in the reference that if the polyalcohols are added without a solvent, good distribution is not possible. The polymer coating formulation therefore preferably contains a hydrophilic organic solvent, e.g. methanol. The use of an organic solvent is not desirable due to its processability and its negative impact to the environment.

Great Britain Patent 2,162,525 (incorporated herein by reference) discloses the addition of finely divided silica to the crosslinked adsorbent resin particles as described in Great Britain Patent 2,119,384, to prevent agglomeration of the resin particles.

What are needed are water absorbent resin particles which have high absorption capacity, low extractables, i.e. water-soluble polymer fraction, and high toughness or gel modulus. Furthermore, what are needed are water absorbent resin particles which have a low tendency to agglomerate. What is further needed is a process for the preparation of such particles, which is environmentally friendly. What are further needed are particles and processes which do not employ the use of materials which may be irritating, or which may be harmful to human health.

SUMMARY OF INVENTION

The invention is surface crosslinked particles of water absorbent resin comprising a carboxyl containing water-absorbent resin wherein the carboxyl containing water-absorbent resin is crosslinked at or near the particle surface by a polyhydroxy compound capable of reacting with the carboxyl moieties of the water-absorbent resin, and the particles have coated on or bound to the surface a nonionic surfactant having an HLB of from about 3 to about 10.

In another embodiment, the invention is a process for the preparation of surface crosslinked water-absorbent resins which comprises A) contacting a hydrogel of the water-absorbent resin with a composition comprising optionally water, a polyhydroxy compound and a surfactant, or a polyhydroxy surfactant, and optionally a water miscible polar solvent under conditions such that the polyhydroxy compound and surfactant, or the polyhydroxy surfactant, coat the absorbent resin particles without substantial penetration into the interior of the absorbent resin particles;

B) drying the mixture of the hydrogel of the water-absorbing resins, and the composition containing the polyhydroxy compound and a surfactant, or the polyhydroxy surfactant, under conditions such that the water, and optional solvent if present, are substantially removed, and the polyhydroxy compound or the polyhydroxy surfactant does not significantly react with the carboxyl moieties of the water-absorbent resin;

C) optionally, reducing the particle size of the dried coated water-absorbent resin by mechanical means; and, D) heating the coated water-absorbent resin under conditions such that the polyhydroxy compound or the polyhydroxy surfactant reacts with the carboxyl moieties of the water-absorbent resin so as to crosslink the surface of the water-absorbent resin particles.

In yet another embodiment, the invention is a water-absorbent structure comprising a synthetic or natural fiber or paper based woven or nonwoven carrier structure and surface crosslinked and surfactant coated water-absorbent resin particles of this invention.

The water-absorbent resin particles of this invention demonstrate high absorption capacities while having low extractable fractions, a high absorbent particle gel toughness, and demonstrate a reduced tendency to agglomerate when wetted. The process for the preparation of the water-absorbent resin particles does not require the presence of organic solvents. Further, the water absorbent resin particles do not require the use of or presence of materials which may be irritating to human skin, or which may be harmful to human health. During processing the water-absorbent particles do not form large agglomerates which require extra and costly processing.

DETAILED DESCRIPTION OF THE INVENTION

Generally, water absorbent resin particles are prepared by a well-known processes. The monomers from which the polymers prepared are polymerized in aqueous solution. Certain additives, such as crosslinking agents and surfactants, may be incorporated into the monomer mixture, which is polymerized. Processes for polymerizing such monomers, thereby forming the polymers from which water absorbent resin particles are derived are described in the patents and patent applications described hereinbefore. The product of the polymerization process is a hydrogel which is a water-swollen form of the polymer. Generally, this hydrogel is subjected to mechanical means of reducing the particle size to granulate the hydrogel. Thereafter, the hydrogel is dried to remove the water. The particles then can be subjected to further mechanical means of particle size reduction and classification including chopping, grinding and sieving. In those embodiments described hereinbefore wherein a crosslinking agent was added after polymerization, the crosslinking agents were added to the dried resin powder. Generally in such situations after addition of the crosslinking agents, the particles are then subjected to conditions under which the crosslinking agents react with a portion of the water-absorbent polymer so as to crosslink the surface of the particles.

Hydrogel as used herein refers to water swollen absorbent resin particles. In preferred embodiments such hydrogels comprise from about 15 to about 90 percent by weight water absorbent polymer, with the remainder comprising water. In a more preferred embodiment the hydrogel comprises from about 30 to about 45 percent water absorbent polymer.

Surface crosslinked refers herein to absorbent resin polymer particles which are contacted with a crosslinking agent after completion of polymerization under conditions such that the particles are coated at or near the surface and the particles are exposed to conditions such that the crosslinker reacts with carboxyl groups at or near the surface of the particle to crosslink the water absorbent resin.

Water-absorbent polymers useful in this invention are water-absorbent polymers which contain carboxyl moieties. Among preferred carboxyl containing water absorbent polymers are hydrolyzates of starch-acrylonitrile graft copolymers, partially neutralized products of a starch-acrylic acid graft copolymers, saponification products of vinyl acetate acrylic ester copolymers, hydrolyzates of acrylonitrile copolymers, crosslinked products of hydrolyzates of acrylonitrile copolymers, hydrolyzates of acrylamide copolymers, crosslinked products of hydrolyzates of acrylamide copolymers, partially neutralized products of polyacrylic acids and crosslinked products of partially neutralized polyacrylic acids.

Especially preferred are alkali metal acrylate-type polymers obtained by copolymerizing 100 parts of an acrylic acid-type monomer composed of from about 1 to about 50 mole percent of acrylic acid and from about 50 to about 99 mole percent of an alkali metal acrylate and from about 0 to about 5 percent by weight of a crosslinkable monomer in aqueous solution in a monomer concentration of at least about 20 percent by weight. In another preferred embodiment the alkali metal acrylate-type polymers are obtained by polymerizing acrylic acid and post neutralizing the polymer with an alkali metal base.

There is no limitation to the amount of the carboxyl groups of the water-absorbing resin. Preferably, at least about 0.01 equivalent of carboxyl groups are present per 100 g of the water-absorbing resin. In the case of the partially neutralized polyacrylic acid, the proportion of the unneutralized portion is preferably from about 1 to about 50 mole percent.

The polyhydroxy compound which is used as a crosslinking agent is a compound which contains at least two hydroxyl groups which are capable or readily reacting with the carboxyl groups of the water-absorbent resin, and which is capable of being dispersed over the surface of a water-absorbent resin particle. Preferably, the polyhydroxy compound used in this invention is selected from the group consisting of glycol, diethylene glycol, triethylene glycol, polyethylene glycols, glycerol, polyglycerol, propylene glycol, dipropylene glycol, tripropylene glycol, polypropylene glycols, diethanolamine, triethanolamine, propane diol butane diol, hydroxy terminated oxyethylene-oxypropylene block copolymers, sorbitan fatty acid esters, polyoxyethylene sorbitan fatty acid esters, trimethylolpropane, pentaerythritol, sorbitol, mannitol, sugars, sugar derivatives, polyoxyethylene sorbitol derivatives, polyoxyethylenelanolin derivatives and the like. More preferred polyhydroxy compounds include diethylene glycol, triethylene glycol, glycerol, propylene glycol, trimethylol propane, pentaerythritol, and sorbitol. Even more preferred are sorbitol and glycerol.

The amount of polyhydroxy hydrocarbon applied to the surface of the adsorbent resin particle is that amount which significantly improves its gel strength as evidenced by an increased absorption under low (AUL) and which does not significantly reduce the absorptive capacity of the resin once the crosslinking has occurred. Preferably the amount of polyhydroxy compound is from about 0.01 to about 10 parts per hundred parts by weight of water-absorbent resin. More preferably from about 0.1 to about 1.0 parts of polyhydroxy compound per 100 parts of water-absorbent resin are used, with from about 0.1 to about 0.3 parts of polyhydroxy compound per hundred parts of water-absorbent resin being most preferred.

The surfactants which may be coated on the surface of, or bound to the surface of the water-adsorbent resin particles are nonionic surfactants having an HLB in the range of from about 3 to about 10 and which are dispersible in water. Preferable surfactants include those selected from the group of sorbitan fatty acid esters, polyoxyethylene sorbitan fatty acid esters, glycerol fatty acid ethers or polyglycerol fatty acid esters, polyoxy ethylene alkyl esters, polyoxyethylene alkylphenol ethers, polyoxyethylene acyl esters and sucrose fatty acid esters or modified surface active polyesters. More preferred surfactants are polyethoxylated sorbitol lanolin derivatives, for example a surfactant available from ICI under the Tradename G1425. A sufficient amount of surfactant is used to facilitate a homogeneous distribution of the crosslinking agent on the surface of the gel particles, to improve the processability of the gel by reducing its stickiness, to reduce the tendency of the dried powder to agglomerate when exposed to humid air or water, and to bind fine dust of the water-absorbent resin.

The surfactant is either adsorbed or coated onto the surface or bound to the surface via chemical interaction. The amount of surfactant used is preferably from about 0.01 to about 2 parts per hundred parts by weight of water-absorbent resin. More preferably from about 0.075 to about 0.5 parts per hundred parts by weight of water-absorbent resin.

A nonionic surfactant having an HLB of about 3 to about 10 which has two or more hydroxy (polyhydroxy containing surfactant) moieties which are capable of reacting with carboxyl moieties can be used both as the polyhydroxy compound and the surfactant. In such a case the hydrogel need only be contacted with such a surfactant and the remainder of the process steps can be carried out. In one aspect the use of such a surfactant is advantageous as it would not migrate into the pores of the hydrogel thus allowing crosslinking at the surface only.

In order to contact the surfactant and the polyhydroxy compound with the hydrogel of water-absorbent resin, a composition of surfactant and polyhydroxy compound, or a composition containing a polyhydroxy surfactant is prepared. The coating composition may comprise the polyhydroxy compound and surfactant, or the polyhydorxy surfactant only. The composition is preferably water-based, and polar organic solvents which are miscible with water may additionally be used. Preferred cosolvents are lower alkanols. Such solutions can contain up to about 99 percent water, or water and solvent, so as to reduce the coating formulation viscosity. The relative amounts of solvents, surfactants and polyhydroxy compound are chosen such that the composition can readily disperse over the absorbent particles to be coated, and to provide a sufficient amount of surfactant and polyhydroxy compound, or polyhydroxy surfactant, to coat the surface of the water-absorbent particles. Preferably, the composition contains from about 0 to about 99 percent by weight water, more preferably from about 20 to about 80 percent by weight water. Preferably the solution contains from about 0 to about 99 percent by weight organic solvent, more preferably from about 0 to about 50 percent by weight organic solvent, and most preferably no organic solvent is used. The amount of surfactant or polyhydroxy surfactant is preferably from about 0.1 to about 99.5 percent by weight, and most preferably from about 5 to about 40 percent by weight. The amount of polyhydroxy compound is from about 0.1 to about 99.5 percent by weight, and most preferably from about 10 to about 50 percent by weight.

A sufficient amount of the composition containing the polyhydroxy compound and surfactant, or polyhydroxy surfactant, is contacted with the water-absorbent resin hydrogel particles to coat a sufficient amount of polyhydroxy hydrocarbon and surfactant, or polyhydroxy surfactant, on the particles to achieve the desired goals described herein. Preferably from about 50 to about 99.98 parts by weight of water-absorbent resin are contacted with from about 0.02 parts to about 50 parts of the composition, and more preferably from about 95 to about 99.8 parts of resin from about 0.2 to about 5 parts of the composition.

In order to prepare the absorbent resin particles of the invention, the absorbent resin in the hydrogel form is contacted with a composition of surfactant and polyhydroxy compound, or polyhydroxy surfactant. The hydrogel is preferably in granular form, with particle sizes of about 2 cm or less being more preferred. The amount of solution used should be that which is sufficient to provide a coating of polyhydroxy compound and surfactant, or the polyhydroxy surfactant, on the absorbent resin particles such that the hereinbefore described aims of the invention are achieved, in particular, high absorption under load, with low extractables, and high absorptive capacity. Further, such coated particles should have processability in the wet and dry form. The absorptive resin hydrogels and coating composition should be contacted under conditions such that the particles can be coated with the surfactant and polyhydroxy compound, or polyhydroxy surfactant, but such that the polyhydroxy compound and surfactant, or polyhydroxy surfactant, do not significantly diffuse into the internal structure of the water-absorbent resin particle. That is the polyhydroxy compound and surfactant, or polyhydroxy surfactant remain on or near the surface of the particle. It is preferable that such contacting should be conducted with some form of mixing, such that adequate distribution of the polyhydroxy compound and surfactant, or polyhydroxy surfactant, on the water-absorbent resin particles can be acheived. Moderate stirring, shaking or even a short distance of conveying in a screw-conveyer is sufficient for such adequate distribution of the solution over the gel particles of the water-absorbent resin, particularly if the hydrogel particles of the water-absorbent resin is at elevated temperatures. The contact time of the solution and the hydrogel particles of the water-absorbent resin should be sufficient to coat the particles with the polyhydroxy compound and surfactant, or polyhydroxy surfactant, but not so long as to allow diffusion of the polyhydroxy compound into the pores or internal structure of the water-absorbent resin particles. Preferably such contact time is from about 5 seconds to about 10 minutes, preferably from about 20 seconds to about 60 seconds. The temperature of contacting can be any temperature at which the polyhydroxy compound or polyhydroxy surfactant does not significantly react with the carboxyl moieties of the absorbent resin polymer. Preferably such temperatures are from about 20° C. to about 100° C., more preferably from about 40° C. to about 70° C. It should be noted that elevated temperatures, i.e. those temperatures above ambient (about 20° C.) improve the speed of coating of the water-absorbent resin particles.

After coating of the water-absorbent resin hydrogel particles, the particles may be optionally subjected to further mechanical particle size reduction. The size of the gel particles after mechanical particle size reduction should be such that homogeneous drying of the particles can occur.

Thereafter, the water-absorbent resin hydrogel particles are subjected to conditions to remove the water and optional solvent. This drying process is used to remove substantially all of the water and optional solvent, such that the water-absorbent resin particles can be further processed, packaged, and incorporated into absorbent structures. The temperature at which the drying takes place is a temperature high enough such that the water, and optional solvent, is removed in a reasonable time period, yet not so high so that the polyhydroxy compound or polyhydroxy surfactant coated on the water absorbent resin particles reacts with the carboxyl moieties of the water-absorbent resin before water is removed. Preferably, the temperature of the water absorbent resin particles during drying is about 175° C. or less. Preferably, the temperature during drying is about 100° C. or more, and more preferably about 150° C. or more. The drying time should be sufficient to remove substantially all of the water and optional solvent. Preferably, a minimum time is about 10 minutes or greater, with about 15 minutes or greater being preferred. Preferably, a maximum drying time is about 60 minutes or less, with about 20 minutes or less being more preferred. In a preferred embodiment, drying is performed under conditions such that water, and optional solvent, volatilizing away from the absorbent resin particles is removed. This can be performed by the use of vacuum techniques or by passing inert gases or air over or through the layers of water-absorbent resin particles. In a preferred embodiment, the drying occurs in dryers in which heated air is blown through or over layers of the water-absorbent resin particles. Preferred dryers are fluidized beds or belt dryers. Alternatively a drum dryer may be used.

In a preferred embodiment, the coated water-absorbent resin particles are then subjected to mechanical particle reduction means. Such means can include chopping, cutting and/or grinding. The object is to reduce the particle size of the water-absorbent resin particles to a particle size acceptable in the ultimate end use. In a preferred mode, the absorbent resin particles are first chopped, and then ground. In a preferred embodiment, the particle size is about 2 mm and more preferably about 0.8 mm or below. Preferably the particles have a size of about 0.02 mm or greater, more preferably about 0.05 mm or greater and more preferably about 0.1 or greater. A significant advantage inherent in the presence of the surfactant, is that it allows the dispersion of the polyhydroxy compound over the entire surface of the water absorbent resin particles after the particles undergo mechanical particle size reduction. This facilitates the production of water-absorbent resin particles which are uniformly crosslinked.

After drying and particle size reduction, the water-absorbent resin particles are then subjected to conditions such that the polyhydroxy compound or polyhydroxy surfactant coated on the surface of the particles reacts with the carboxyl groups of the water absorbent resin so as to crosslink the water-absorbent resin particles at or near the surface of the particle. Conditions for such crosslinking are such that crosslinking occurs without adversely affecting the water-absorbent resin and its properties. The coated water-absorbent resin particles is preferably heated to a temperature of about 150° C. or above, more preferably about 170° C. or above, and most preferably about 175° C. or above to crosslink the surface of the absorbent particles. The temperature should not be so high as to cause the absorbent resin polymer to degrade. Preferably the temperature is about 240° C. or below, more preferably about 210° C. or below, and most preferably about 190° C. or below. The time period for this exposure to elevated temperatures should be sufficient for the polyhydroxy compounds or polyhydroxy surfactant present at or near the surface of the absorbent resin to react with carboxyl groups. Preferably, at least about 5 minutes exposure and most preferably at least about 15 minutes exposure is used. If the exposure time is too long it becomes uneconomical and risk is run that the absorbent resin may be damaged. Preferably the maximum time of heating is about 75 minutes or less, preferably about 60 minutes or less. Preferably this crosslinking is performed in air, and more preferably in the presence of flowing air, such as in a fluidized bed reactor or a plate dryer.

It is important to recognize that the extent of crosslinking of the water-absorbent resin particles significantly affects the properties of the ultimate absorbent resin. If the crosslinking is too high the absorptive capacity of the resin significantly drops. If there is little or no crosslinking, the toughness of the gel is significantly reduced, and therefore its ability to stand up under load and retain absorbed material under load is significantly reduced.

During drying or surface crosslinking the water absorbent resin particles may form agglomerates. Thus, after crosslinking the water absorbent resin particles may be subjected to mechanical means for breaking up the agglomerates. Such means can involve grinding, chopping, cutting or the like.

As there is balance of the absorptive capacity and soluble polymer fraction against the toughness and absorption under load, it is the objective of this invention to maximum the absorption under load and minimize the soluble polymer fraction, i.e. extractables. One measure, is to examine the relative ratio of the absorption under load to the percent extractables. The higher this number is, the more more successful the invention is in maximizing the properties of the water-absorbent resin. Preferably, this ratio is about 2 or greater, more preferably about 3 or greater, and most preferably about 4 or greater. It is also preferred that the resins have an absorption under load of about 15 g/g or greater, more preferably about 28 g/g or greater. It is further preferable that the resins have a percent extractables level of about 18 or less, more preferably about 14 or less, and most preferably about 10 or less.

The crosslinked surfactant coated water-absorbent resin particles of this invention can be used in any use wherein absorption and binding of aqueous based fluids is desired. In a preferred embodiment, the absorbent resin particles of this invention are mixed into or attached to a structure of absorbent material such as synthetic or natural fibers or paper based woven or non-woven fibers etc. to form a structure. In such structure the woven or non-woven structure functions as a mechanism for wicking and transporting via capillary action the fluid to the water-absorbent resin particles which bind and retain such fluids. Examples of such structures are diapers, adult incontinence structures, sanitary napkins and the like.

SPECIFIC EMBODIMENTS OF THE INVENTION

The following examples are included to illustrate the invention, and do not limit the scope of the claims. Unless otherwise stated all parts and percentages are by weight.

Example 1

293 g of 99% pure acrylic acid is partly neutralized with 553 g of a 20% active aqueous caustic solution in a jacketed glass reactor. To this monomer solution are added 1.76 g of trimethylolpropane triacrylate (TMPTA), 1.6 g of polyvinylalcohol and 0.18 g of a 40% active diethylene triamine pentaacetate solution (Versenex* 80 *Trademark of The Dow Chemical Company) and the solution is well mixed. This monomer mix is transferred into a reactor which is equipped with mixing devices capable of mixing the polymerizing mass sufficiently and breaking the polymer gel which is obtained by polymerization. The glass reactor and the line to the reactor is flushed into the polymerizing reactor by an additional 160 g of deionized water. The monomer solution is deoxygenated by purging it with nitrogen. Polymerization initiation is achieved by adding successively 5 g of a 10% aqueous solution of sodium persulfate, 0.98 g of a 15% aqueous solution of hydrogenperoxide and 4.4 g of a 1% aqueous ascorbic acid solution. The exothermic polymerization reaction heats the mixture up to approximately 90°–100° C. After cooling down to 70° C. the gel is held under nitrogen atmosphere at 70° C. for one hour.

The aqueous polymer gel is granulated to particles having a size of between approximately 1 and 5 mm with the aid of a meat mincer (disc holes 5 mm) and a part of it is dried in a hot air stream of 160° C. for approximately 20 min. The polymer is ground in a knife cutter and sieved. The particle size fraction between 0.595 and 0.297 mm (30–50 mesh) is used for performance and quality analysis. For gel strength measurement the fraction 0.297 to 0.177 mm (50–80 mesh) is used.

The product SAP1 is obtained. Performance and quality of produced polymers prepared are measured by the following methods.

Centrifuged Capacity 200 mg of water-absorbent resin particles are place within a sealable tea bag (63.5×76.2 mm), immersed for 30 minutes into a 0.9% saline solution and then centrifuged for three minutes at 1600 rpm. The weight ratio of saline solution absorbed to water-absorbent resin particles is the absorbency capacity (cc).

Absorption Under Load

A nylon screen (50×50 mm; 325 mesh) is put on top of perforated metal plate (holes with 5 mm) followed by a filter paper and finally by a stainless steel cylinder, whose both ends are open, of 26 mm inner diameter, 37 mm outer diameter and a height of 50 mm. 120 mg of water-absorbent resin particles are placed into the cylinder and evenly distributed, covered by a non-woven sheet of a diameter of 26 mm and finally pressed down with a teflon piston of 26 mm diameter which carries the weight. The total weight of piston and cylinder is 100 g. The metal plate with the product in the cylinder on top is immersed into the 0.9% saline solution such, that the nylon screen and the water surface have the same level so that the filter paper and the water-absorbent resin particles are able to absorb water without any static pressure.

A soak time of one hour is applied. The plate is removed from the water reservoir and the excess water in the holes of the plate and in the nylon screen is soaked up by paper tissues. Then the weight is removed from the swollen gel and the gel is weighed. The weight ratio of saline solution absorbed under load to water-absorbent resin particles is the absorption under load (AUL).

Extractables 1 g of water-absorbent resin particles and 185 ml of 0.9% saline solution are placed in an 250 ml jar which is capped and put on a shaker for 16 hours. A part of the extraction solution is filtered. With the aid of a Metrohm Titroprocessor the pH of a defined volume of the filtrate is adjusted to pH 10 by 0.1 n NaOH and finally titrated to pH 2.7 by 0.1 normal hydrochloric acid, to determine the amount of residual monomer which is in the filtrate.

Caking in Humid Air 10 g of water-absorbent resin particles (0.595–0.297 mm) are put into a 40 ml crystallizing dish and placed onto the ceramic plate of a desiccator. The lower part of the desiccator is filled with water which is in contact with filter papers which covers the inner side of the desiccator to assure maximum humidity of the test atmosphere. The water-absorbent resin particles stay in this environment at room temperature for 24 hours. The extent of agglomeration which may be formed, particularly on the product surface, is checked with a spatula.

Example 2

The same procedure as applied in Example 1 is applied to make water-absorbent resin particles (SAP 2) except that 0.64 g of crosslinker (TMPTA) and 4.1 g of a 10% aqueous solution of sodiumpersulfate are added to the monomer mix.

Example 3

200 g of minced water-absorbent resin particles gel as obtained in Example 1 is coated by mixing the gel with 350 mg of a 20% aqueous emulsion of the polyethoxylated sorbitol lanolin derivative, designated G1425, and drying the gel in an hot air stream of 160° C. for 20 min. The resin prepared is designated SAP 3.

Example 4

The same procedure is followed as in Example 3 except that a coating formulation consisting of 350 mg of an 20% aqueous emulsion of polyethoxylated sorbitol lanolin derivative and 70 mg of glycerol is used. A water absorbent resin designated SAP 4 is obtained.

Examples 5–7

15 g each of the SAP 1, SAP 3 and SAP 4 are heated in an air stream of 200° C. for 10 minutes. Water-absorbent resin particle samples designated SAP 5, SAP 6 and SAP 7 are obtained.

Examples 8–12

Water-absorbent resin particle gel as obtained in Example 2 is subjected to the same treatment as the Water-absorbent resin particle gel SAP 1 by the experiments described in the Examples 3–7. Water-absorbent resin particle samples designated SAP 8, SAP 9, SAP 10, SAP 11 and SAP 12 are obtained.

Example 13

30 g of SAP 2 is coated by contacting with a formulation consisting in 112 mg of a 20% active aqueous emulsion of the surfactant G1425 and 60 mg of glycerol and intimate mixing 15 g of the coated polymer powder is then subjected to a hot air stream as described in the Examples 5–7. The water-absorbent resin particle sample designated SAP 13 is obtained.

Example 14

299 g of minced water-absorbent resin particle gel as obtained in Example 2 is coated with a formulation consisting in 350 mg of a 20% active aqueous solution of G1425 and 105 mg of sorbitol and dried as described in Example 3. After grinding and sieving as in Example 1 the polymer is subjected to a hot air stream of 190° C. for 14 minutes. The water-absorbent resin particle sample designated SAP 14 is obtained.

The results are compiled in Table I.

TABLE I

| SAP | Coating[1] Surfactant/glycerol gel | Coating[1] Surfactant/glycerol powder | Heat Treatment (°C./min) | Centrifuge Capacity (CC) (g/g) | Absorption under Load (AUL) (g/g) 30 min | Absorption under Load (AUL) (g/g) 5 min | Percent Extractables | Ratio AUL Extr. | Caking resistance[2] |
|---|---|---|---|---|---|---|---|---|---|
| 1[3] | — | — | — | 30.07 | 23.3 | 10.0 | 12.8 | 1.82 | 4.5 |
| 3[3] | 1000/0 | — | — | 31.2 | 25.0 | | 10.2 | 2.45 | 3.5 |
| 4 | 1000/1000 | — | — | 30.0 | 25.0 | | 10.2 | 2.45 | 3.5 |
| 5[3] | — | — | 200/10 | 29.0 | 27.0 | | 11.3 | 2.39 | 4.5 |
| 6 | 1000/0 | — | 200/10 | 30.0 | 25.8 | | 9.4 | 2.74 | 3 |
| 7 | 1000/1000 | — | 200/10 | 27.3 | 30.8 | 20.5 | 7.9 | 3.90 | 1.5 |
| 2[3] | — | — | — | 40.7 | 15.0 | | 19.5 | 0.77 | 5 |
| 8[3] | 1000/0 | — | — | 41.3 | 13.3 | | 20.2 | 0.66 | 3.5 |
| 9 | 1000/1000 | — | — | 38.6 | 15.8 | | 17.3 | 0.91 | 3.5 |
| 10[3] | — | — | 200/10 | 41.0 | 18.0 | | 19.5 | 0.92 | 4.5 |
| 11 | 1000/0 | — | 200/10 | 41.5 | 23.3 | | 20.1 | 1.16 | 2.5 |
| 12 | 1000/1000 | — | 200/10 | 39.7 | 24.0 | | 11.3 | 2.12 | 1.5 |
| 13[3] | — | 1000/2000 | 200/10 | 39.0 | 19.7 | | 20.2 | 0.95 | 1.5 |
| 14 | 750/1500 | — | 190/14 | 37.8 | 28.9 | | 13.8 | 2.0 | 1.5 |

[1])concentrations in ppm (b.o. dry SAP)
[2])1 = excellent 5 = insufficient
[3])Not an example of invention

We claim:
1. Surface crosslinked particles of water-absorbent resin comprising a crosslinked carboxyl containing, solution polymerized, water-absorbent resin wherein the resin comprises a polymer of acrylic or methacrylic acid in which from about 50 to about 99 percent of the carboxyl moieties are neutralized; wherein the crosslinked carboxyl containing water-absorbent resin is crosslinked at or near the particle surface by a nonionic surfactant which is a polyethoxylated sorbitol-lanolin derivative having an HLB of from 3 to 10, in the presence of from about 0.01 to about 10 parts by weight of a polyhydroxy compound based on 100 parts of the water-absorbent resin, the polyhydroxy compound being capable of reacting with the carboxyl moieties which is glycerol or sorbitol and the water-absorbent resin particles have coated or bound on their surface from about 0.01 to about 2.0 parts by weight of the surfactant based on 100 parts of the water-absorbent resin the nonionic surfactant.

2. A process for the preparation of surface crosslinked absorbent resin particles which comprises
   A) contacting particles of a hydrogel of crosslinked carboxyl containing water-absorbent resins with a nonionic surfactant having an HLB of from 3 to 10, optionally in the presence of a composition comprising a polyhydroxy compound which is ethylene glycol, diethylene glycol, triethylene glycol, polyethylene glycol, glycerol, polyglycerol, propylene glycol, dipropylene glycol, tripropylene glycol, polypropylene glycol, propane diol butane diol, diethanolamine, triethanolamine, trimethylolpropane, pentaerythritol, sorbitol or mannitol, optionally water and optionally a water miscible polar solvent, under conditions such that the surfactant and optionally the polyhydroxy compound, coat the water-absorbent resin particles without significant penetration into the interior of the absorbent resin particles;

B) drying the mixture of the hydrogel of the water-absorbent resin, and composition containing the surfactant and optionally the polyhydroxy compound, under conditions such that the water, and optional solvent if present, are removed and the surfactant and optionally the polyhydroxy compound does not significantly react with the carboxyl moieties of the water-absorbent resin;

C) optionally, reducing the particle size of the dried coated absorbent resin by mechanical means; and D) heating the coated water-absorbent resin particles under conditions such that the surfactant and optionally the polyhydroxy compound react with the carboxy moieties of the water-absorbent resin so as to crosslink the surface of the water-absorbent resin particles.

3. A process according to claim 2 wherein the composition containing the polyhydroxy compound and surfactant comprises i) from about 0 to about 99 parts by weight water;

ii) from about 0 to about 99 parts by weight polar organic solvent;

iii) from about 0.1 to about 99 parts by weight of surfactant;

iv) from about 1 to about 99 parts by weight of polyhydroxy compound.

4. A process according to claim 3 wherein from about 50 to about 99.98 parts of water-absorbent resin hydrogel by weight and from about 0.02 to about 50 parts by weight of the solution containing the polyhydroxy compound and surfactant, are contacted.

5. A process according to claim 4 wherein

A) the hydrogel of the water-absorbent resin and the composition comprising polyhydroxy compound and surfactant, are contacted for a time of from about 0.5 minutes to about 10 minutes at a temperature of from about 20° C. to about 150° C.;

B) the mixture of the hydrogel of water-absorbent resin having coated thereon the composition comprising polyhydroxy compound and surfactant, are dried at from about 100° to about 175° C. for about 10 to about 60 minutes;

C) the particle size of the dried coated water-absorbent resin particles is reduced to less than about 2 mm;

D) the coated water-absorbent resin particles are heated to a temperature of from about 175° to about 210° C. for from about 5 to about 75 minutes such that the polyhydroxy compound reacts with the carboxyl moieties at or near the surface of the water-absorbent resin particles to crosslink the water-absorbent resin particles at or near the surface.

* * * * *